United States Patent
Ptchelintsev

(10) Patent No.: US 8,551,956 B2
(45) Date of Patent: Oct. 8, 2013

(54) COMPOSITIONS CONTAINING PEPTIDES WITH NON-NATURAL AMINO ACIDS AND METHODS OF USE

(75) Inventor: Dmitri S. Ptchelintsev, Jersey City, NJ (US)

(73) Assignee: Avon Products, Inc., New York, NY (US)

( * ) Notice: Subject to any disclaimer, the term of this patent is extended or adjusted under 35 U.S.C. 154(b) by 447 days.

(21) Appl. No.: 12/158,188

(22) PCT Filed: Feb. 28, 2007

(86) PCT No.: PCT/US2007/005216
§ 371 (c)(1),
(2), (4) Date: Jun. 19, 2008

(87) PCT Pub. No.: WO2007/100874
PCT Pub. Date: Sep. 7, 2007

(65) Prior Publication Data
US 2009/0082252 A1    Mar. 26, 2009

Related U.S. Application Data

(60) Provisional application No. 60/777,415, filed on Feb. 28, 2006.

(51) Int. Cl.
*A61K 38/06*    (2006.01)
(52) U.S. Cl.
USPC .................... 514/21.9; 530/331; 530/332
(58) Field of Classification Search
None
See application file for complete search history.

(56) References Cited

U.S. PATENT DOCUMENTS

| | | |
|---|---|---|
| 6,060,043 A | 5/2000 | Hayden et al. |
| 6,235,291 B1 | 5/2001 | De La Charriere et al. |
| 6,245,342 B1 | 6/2001 | Golz-Berner et al. |
| 6,358,929 B1 | 3/2002 | Mahe et al. |
| 6,372,717 B1 | 4/2002 | Greff |
| 6,566,115 B1 | 5/2003 | Weisgerber et al. |
| 6,566,330 B1 | 5/2003 | Dix |
| 6,620,419 B1 | 9/2003 | Lintner |
| 6,777,389 B1 | 8/2004 | Mitts et al. |
| 6,821,524 B2 | 11/2004 | Marini |
| 6,852,699 B1 | 2/2005 | Schonrock et al. |
| 2003/0148927 A1 | 8/2003 | Patt |
| 2004/0120918 A1 | 6/2004 | Lintner et al. |
| 2004/0141339 A1 | 7/2004 | Kotsuji et al. |
| 2004/0229808 A1 | 11/2004 | Owen |
| 2005/0118124 A1 | 6/2005 | Reinhart et al. |
| 2005/0124545 A1 | 6/2005 | Dal Farra et al. |
| 2005/0142092 A1 | 6/2005 | Lintner |
| 2005/0148495 A1 | 7/2005 | Lambert, Jr. et al. |
| 2005/0187164 A1 | 8/2005 | Pinel |
| 2007/0259819 A1 | 11/2007 | Bakala et al. |

FOREIGN PATENT DOCUMENTS

| | | |
|---|---|---|
| JP | 07304649 A | 11/1995 |
| WO | 03/086313 A2 | 10/2003 |
| WO | 2005/090389 A2 | 9/2005 |
| WO | 2007/093839 A1 | 8/2007 |
| WO | WO2007093839 * | 8/2007 |

OTHER PUBLICATIONS

Fournier et al.; Sequencing of a branched peptide using matrix-assisted laser desorption/ionization time-fo-flight mas spectrometry; J. Mass Spectrometry, Jan. 2001, vol. 35, No. 12, pp. 1425-1433, scheme I.

* cited by examiner

*Primary Examiner* — Christina Bradley
(74) *Attorney, Agent, or Firm* — David M. Joyal; Joan M. McGillycuddy

(57) ABSTRACT

The invention relates generally to peptides comprising one or more non-natural amino acids residues and their use in cosmetic and personal care compositions.

8 Claims, No Drawings

COMPOSITIONS CONTAINING PEPTIDES WITH NON-NATURAL AMINO ACIDS AND METHODS OF USE

RELATED APPLICATIONS

This application claims priority to International Application Serial No. PCT/US07/05216 filed Feb. 28, 2007, which claims priority U.S. provisional patent application Ser. No. 60/777,412, filed Feb. 28, 2006, the contents of which are hereby incorporated by reference in their entirety.

REFERENCE TO A SEQUENCE LISTING

As required under 37 C.F.R. §1.52(e)(5), this application incorporates by reference the Sequence Listing material submitted in the 4 kB text file identified by the file name: SC89U-USSeqList_ST25.txt and created on Sep. 3, 2010.

FIELD OF INVENTION

The invention relates generally to peptides comprising one or more non-natural amino acids residues and their use in cosmetic and personal care compositions.

BACKGROUND OF THE INVENTION

A variety of natural and synthetic peptides have found widespread use in cosmetic compositions. Typically, peptides are included in cosmetics for their functional attributes such as enzyme inhibition, antiviral and antibacterial activity. Examples of the use of peptides in cosmetic applications are provided in the following literature.

U.S. Patent Publication No. 2005/0142092 A1 describes cosmetic compositions comprising hesperidin and an angiotensin converting enzyme (ACE) inhibitor dipeptide, such as H-Val-Trp-OH, or an oligopeptide, exemplified by H-Gly-Gln-Pro-Arg-OH (SEQ ID NO: 1) or palmitoyl-Gly-Gln-Pro-Arg-OH (SEQ ID NO: 2), stated to be useful for reducing bags and circles under the eyes.

U.S. Patent Publication No. 2005/0124545 A1 relates to the use of a family of peptides, such as Arg-Asp-Phe-Thr-Lys-Ala-Thr-Asn-Ile-Arg-Leu-Arg-Phe-Leu-Arg (SEQ ID NO: 3), in cosmetic compositions. The peptides are said to reduce cutaneous aging.

U.S. Patent Publication No. 2004/0229808 A1 discloses skin care compositions comprising a peptide of 5 to 22 amino acids having at least 50% phenylalanine, leucine, alanine, and lysine residues (FLAK peptides), for antibacterial, antifungal, anticancer, stimulation and proliferation applications, and wound healing applications.

U.S. Patent Publication No. 2004/0141939 A1 discloses peptides comprising the sequence Leu-Asp-Ala-Pro (SEQ ID NO: 4), as exemplified by Lys-Leu-Asp-Ala-Pro-Thr (SEQ ID NO: 5), and their cosmetic and dermatological applications. The peptides are said to promote adhesion between skin cells and cure or prevent symptoms of aging skin.

U.S. Patent Publication No. 2004/0120918 A1 provides cosmetic compositions comprising a polypeptide having anti-aging activity and a ceramide capable of providing an improvement in the anti-aging activity of the polypeptide. The peptides have an amino acid sequence of from 3 to 12 amino acids in length, such as Val-Gly-Val-Ala-Pro-Gly (SEQ ID NO: 6).

U.S. Pat. No. 6,821,524 describes the use of the small, naturally occurring polypeptide thymosin-beta-4 (TB4) in cosmetic compositions for improving the appearance of aged or damaged skin. Vascular endothelial growth factor (VEGF) and transforming growth factor beta 1 (TGFB) peptides are also stated to be useful for inclusion in the described cosmetic compositions.

U.S. Pat. No. 6,852,699 discloses the use of peptides based on the structure Val-Val-Arg-Pro (SEQ ID NO: 7) for treating undesired skin pigmentation.

U.S. Pat. No. 6,777,389 describes cosmetic compositions comprising peptides corresponding to or homologous with portions of endogenous elastin, including Valine-Valine-Proline-Glutamine (SEQ ID NO: 8), Valine-Alanine-Alanine-Arginine-Proline-Glycine (SEQ ID NO: 9), Leucine-Glycine-Alanine-Glycine-Glycine-Alanine-Glycine (SEQ ID NO: 10), and Valine-Glycine-Valine-Hydroxyproline-Glycine (SEQ ID NO: 11), and their use enhancing the appearance of skin suffering from problems associated with deficient elastin.

U.S. Pat. No. 6,620,419 discloses cosmetic compositions comprising polypeptides, exemplified by Lys-Thr-Thr-Lys-Ser (SEQ ID NO: 12), which are stated to induce synthesis of collagen and glycosaminoglycans to treat skin aging.

U.S. Pat. No. 6,372,717 discloses cosmetic compositions comprising synthetic lipophile derivatives of Tyr-Arg peptides, including N-Acetyl-L-Tyr-L-Arg-O-hexadecyl, for relieving sensations of irritation, mild pain, effects of heat, cold, abrasion or mechanical attacks on the skin.

U.S. Pat. No. 6,245,342 discloses the use in cosmetic compositions of peptides comprising His-Phe-Arg-Trp (SEQ ID NO: 13) derived from α-MSH (melanocyte stimulating hormone). The cosmetic compositions are stated to have melanogenesis-stimulating and anti-inflammatory properties.

U.S. Pat. No. 6,358,929 describes the use of a peptide containing the sequence Lysine-Proline-Valine as an additive in cosmetic compositions for preventing or reducing the intolerance reactions linked to a contact hypersensitivity.

U.S. Pat. No. 6,235,291 describes the use of the peptides sendide (Tyr D-Phe Phe D-His Leu Met NH$_2$; SEQ ID NO: 14) and spantide II (D-NicLys Pro 3-Pal Pro D-Cl$_2$ Phe Asn D-Trp Phe D-Trp Leu Nle NH$_2$; SEQ ID NO: 15) as Substance P antagonists in cosmetic products for treating sensitive skin.

U.S. Pat. No. 6,235,291 relates to the use of a peptide (Gly Ile Gly Asp Pro Val Thr Cys Leu Lys Ser Gly Ala Ile Cys His Pro Val Phe Cys Pro Arg Arg Tyr Lys Gln Ile Gly Thr Cys Gly Leu Pro Gly Thr Thr Cys Cys Lys Lys Pro; SEQ ID NO: 16) having activity against bacteria, mycota and/or viruses and its use in cosmetic compositions.

Other peptide additives for cosmetic compositions include soya peptides for inhibiting elastase, plant peptides for inhibiting collagenase, copper complexes of peptides such as glycyl-L-histidyl-L-lysine, L-valyl-L-histidyl-L-lysine, and L-alanyl-L-histidyl-L-lysine (U.S. Patent Publication No. 2003/0148927), ovotransferrin peptides for inhibiting proteases which degrade elastin or collagen, and the anti-wrinkle peptides acetyl hexapeptide-3 having the structure acetyl glutamyl-glutamyl-methyonyl-glutamyl-arginyl-arginylamide (SEQ ID NO: 17; U.S. Patent Publication No. 2005/0118124 A11), palmitoyl oligopeptide and palmitoyl pentapeptide-3 having the sequence Lys-Thr-Thr-Lys-Ser (SEQ ID NO: 18).

Other interesting peptides are described in, for example, U.S. Pat. Nos. 6,566,330, 6,060,043 and 6,566,115, U.S. Patent Publication No. 2005/0187164 A1 and 2005/0148495 A1, and published PCT applications WO 2005/097060 A1 and WO 03/086313 A2, the disclosures of which are hereby incorporated by reference.

Despite the desirability of incorporating peptides in cosmetics, there are certain disadvantages associated with their use. For example, active peptide agents may suffer from poor efficacy of use due to, for instance, their conformational flexibility and/or the easy digestion of peptides by proteases at the sites of intended action. Further, efficacy may be hindered due to the difficulty with which peptides are transported across membranes such as skin and their poor solubility in many cosmetic vehicles. Additionally, the risk of immunogenic reaction to peptides also presents a concern in cosmetic formulation.

It is therefore an object of the invention to provide novel peptides for cosmetic applications which provide enhanced efficacy.

It is another object of the invention to provide novel peptides for cosmetic applications which provide resistance to proteolytic degradation.

It is yet another object of the invention to provide novel peptides for cosmetic applications which decrease the risk of immunogenic reaction.

SUMMARY OF INVENTION

In accordance with the foregoing objectives and others, the present invention provides novel peptides comprising one or more non-naturally occurring amino acids having cosmetically beneficial properties.

One aspect of the invention provides peptides comprising non-natural amino acids having the sequence of formula I:

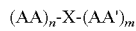

$(AA)_n\text{-}X\text{-}(AA')_m$     I where AA and AA' are independently an amino acid or peptide comprising amino acids selected from the naturally occurring amino acids L-alanine, L-valine, L-leucine, L-isoleucine, L-proline, L-tryptophan, L-phenylalanine, L-methionine, glycine, L-serine, L-tyrosine, L-threonine, L-cysteine, L-asparagine, L-glutamine, L-aspartic acid, L-glutamic acid, L-lysine, L-arginine, and L-histidine;

"n" and "m" are independently an integer from 0 to about 20; and

X represent a non natural amino acid of formula II or a peptide fragment comprising one or more non natural amino acids of formula II optionally including one or more natural amino acids:

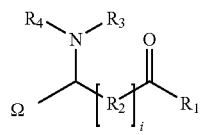

II where $R_1$ represents a peptide bond to an adjacent amino acid of the group AA' or, in the case of cyclic peptides, $R_1$ represents a peptide bond to the terminal residue of the group AA or an amino-functionalized side chain of a residue within the group M, or where X is a terminal amino acid residue of the type m=0, $R_1$ is typically hydroxyl, but may be any other functionality, including, for example, hydrogen, a protecting group, activating group or a lipophilic group such as a moiety selected from the group consisting of substituted or unsubstituted $C_1$ to $C_{20}$ branched, straight chain, or cyclic alkoxy, aryloxy, and the like;

$R_2$, when present, provides amino acids having $NH_2$ groups on carbons atoms other than the α-carbon (the carbon atom adjacent the carboxyl group), including for example, the β or γ carbons, and may therefore be any spacer group and in particular a moiety selected from the group consisting of substituted or unsubstituted branched or straight chain $C_1$-$C_6$ alkyl, alkenyl, alkynyl, aryl, heteroaryl, or alkyl-aryl groups, including without limitation, linear alkyl moieties of the form —$(CH_2)_a$— where "a" is an integer from 1 to 10, including, for example, —$CH_2$—, —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 10, including for example, —$CH_2O$— or —$OCH_2$—, —$CH_2CH_2O$— or —$OCH_2CH_2$—, —$CH_2CH_2CH_2O$— or —$OCH_2CH_2CH_2$—; —$O(CH_2)_aO$— where "a" is as defined above; or a moiety of the form —$(CH_2)_bO(CH_2)_c$—, —$(CH_2)_bS(CH_2)_c$—, or —$(CH_2)_bNR^a(CH_2)_c$— wherein "b" and "c" are independently an integer from 0 (zero) to 10 and $R^a$ is an alkyl, alkenyl, alkynyl, aryl, heteroaryl, or alkyl-aryl group;

"i" represents an integer from 0 (zero) to 3;

$R_3$ and $R_4$ may independently represent bonds to adjacent amino acids or may independently selected from the group consisting of hydrogen, substituted or unsubstituted branched or straight chain $C_1$-$C_{20}$ alkyl, alkenyl, alkynyl, aryl, heteroaryl, alkyl-aryl groups, acyl, or N-protecting groups, and will preferably be hydrogen, methyl, ethyl, propyl, acetyl, or, in the case where X is a terminal residue of the type n=0, $R_3$ and $R_4$ are each preferably hydrogen, acetyl, N-protecting group, or a lipophilic group such as a moiety selected from the group consisting of substituted or unsubstituted $C_1$ to $C_{20}$ branched, straight chain, or cyclic alkyl, alkenyl, aryl, heteroaryl, and the like or substituted or unsubstituted $C_1$ to $C_{20}$ branched or straight chain acyl; or $R_3$ and $R_4$ together may from a cyclic alkyl, aryl, heteroalkyl, or heteroaryl, group having between 3 and 6 carbon atoms; or $R_3$ and $R_4$ may independently, together with $R_2$ or Ω form a cyclic alkyl, aryl, heteroalkyl, or heteroaryl, group having between 3 and 6 carbon atoms;

Ω is selected from hydrogen; hydroxyl; amino; halogen; caboxy, carboxamide, substituted or unsubstituted branched, straight chain or cyclic $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, bicyclic alkyl, aryl, or heteroaryl, and combinations thereof; wherein the foregoing radicals may be substituted with any moiety, including, for example, alkyl, alkkoxy, aryl, aryloxy, heteroaryl, heteroaryloxy, hydroxyl; amino; cyano; halogen; oxo, oxa, caboxy, carboxamide, and combinations thereof;

with the proviso that X does not represent solely a naturally occurring amino acid in the case where neither AA or AA' comprise a non-naturally occurring amino acid of formula II.

In another interesting embodiment of the peptides of formula I, AA and AA' may independently represent a non-naturally occurring amino acid of formula II, or AA and AA' may independently represent a peptide fragment comprising one or more non-naturally occurring amino acids defined by formula II. In a further embodiment, any of AA, AA', and X may further include spacer groups which are not amino acids disposed between adjacent amino acid residues. When present, the spacer groups are typically selected from substituted or unsubstituted branched or straight chain $C_1$-$C_6$ alkyl, alkenyl, alkynyl, aryl, heteroaryl, alkyl-aryl, alkyl-aryl-alkyl, and aryl-alkyl-aryl groups, including without limitation, linear alkyl moieties of the form —$(CH_2)_a$— where "a" is an integer from 1 to 20, including, for example, —$CH_2$—, —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 20, including for example, —$CH_2O$— or —OCH₂—, —CH₂CH₂O— or —OCH₂CH₂—, —CH₂CH₂CH₂O— or —OCH₂CH₂CH₂—; —O(CH₂)ₐO— where "a" is as defined above; or a moiety of the form —(CH₂)ᵦO(CH₂)ᵧ—, —(CH₂)ᵦS(CH₂)ᵧ—, or —(CH₂)ᵦNRᵃ(CH₂)ᵧ— wherein "b" and "c" are independently an integer from 0 (zero) to 20 and Rᵃ is an optionally substituted alkyl, alkenyl, alkynyl, aryl, heteroaryl, or alkyl-aryl group; and wherein the spacer group optionally includes fictionalization at either terminal end, or both terminal ends, with functional groups selected from the group consisting of —O—, —S—, —NRᵃ—, —NRᵃ—(C=O)—, —O—(C=O)—, —O—(C=O)—O—, and —O—(SO₂)—, where Rᵃ is as defined above.

In another aspect of the invention, peptides are selected from the groups consisting of: (i) peptides comprising one or more amino acids of formula II; (ii) peptides comprising only amino acids of formula II; (iii) peptides comprising one or more amino acids of formula II and further including one or more spacer moieties as defined above; and (iv) peptides comprising only amino acids of formula II and further including one or more spacer moieties as defined above.

Another aspect of the invention provides cosmetic compositions for topical use comprising one or more of the peptides of the invention in a cosmetically acceptable carrier.

Yet another aspect of the invention provides a method for ameliorating and/or preventing signs of human skin photo- and intrinsic aging comprising topically applying the cosmetic compositions of the invention to the skin.

These and other aspects of the present invention will become apparent to those skilled in the art after a reading of the following detailed description of the invention, including the illustrative embodiments and examples.

DETAILED DESCRIPTION

As used herein, all terms are intended to have their ordinary meaning in the art unless specifically defined. The term "amino acid" is intended to include naturally occurring amino acids as well as non-naturally occurring amino acids and expansively includes any small molecule having at least one carboxyl group and at least one primary or secondary amine group capable of forming a peptide bond. The term "peptide" is intended to include any molecule having at least one peptide bond and therefore includes di-peptides, tri-peptides, oligopeptides, and polypeptides having up to about 20 amino acid residues. The term "peptide" also embraces structures having one or more linkers, spacers, or terminal groups which are not amino acids.

i. Peptides

The peptides of the invention have the sequence of formula I:

$$(AA)_n\text{-}X\text{-}(AA')_m \qquad \qquad I$$

where AA and AA' are independently an amino acid or peptide comprising amino acids selected from the naturally occurring amino acids shown in Table 1:

TABLE 1

| Amino acid | Structure | Three-letter code | Single-letter code |
|---|---|---|---|
| L-alanine | 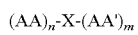 | Ala | A |
| L-valine | 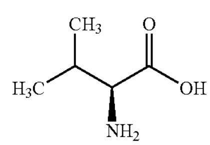 | Val | V |
| L-leucine | 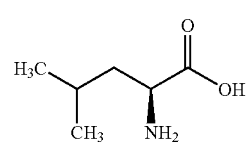 | Leu | L |
| L-isoleucine | 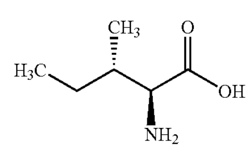 | Ile | I |
| L-proline | 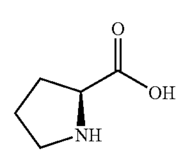 | Pro | P |

TABLE 1-continued

| Amino acid | Structure | Three-letter code | Single-letter code |
|---|---|---|---|
| L-tryptophan | 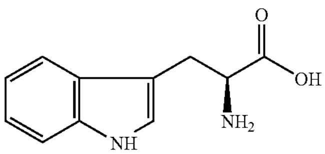 [SMILES: N[C@@H](Cc1c[nH]c2ccccc12)C(=O)O] | Trp | W |
| L-phenylalanine | 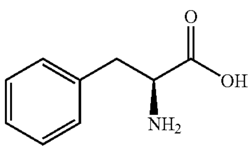 [SMILES: N[C@@H](Cc1ccccc1)C(=O)O] | Phe | F |
| L-methionine | 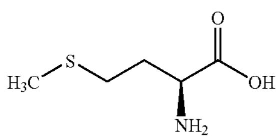 | Met | M |
| glycine | 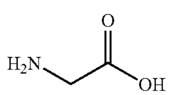 | Gly | G |
| L-serine | 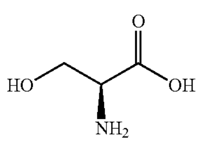 | Ser | S |
| L-tyrosine | 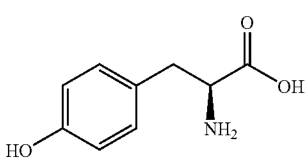 [SMILES: N[C@@H](Cc1ccc(O)cc1)C(=O)O] | Tyr | Y |
| L-threonine | 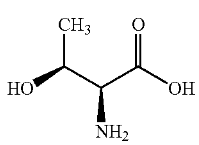 | Thr | T |
| L-cysteine | 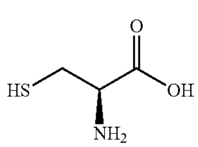 | Cys | C |
| L-asparagine | 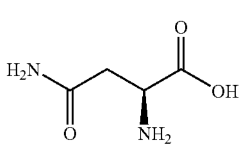 | Asn | N |
| L-glutamine | 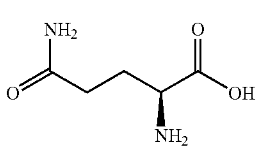 | Gln | Q |

TABLE 1-continued

| Amino acid | Structure | Three-letter code | Single-letter code |
|---|---|---|---|
| L-aspartic acid | 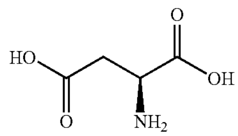 | Asp | D |
| L-glutamic acid | 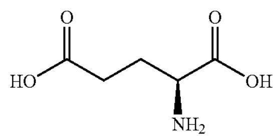 | Glu | E |
| L-lysine | 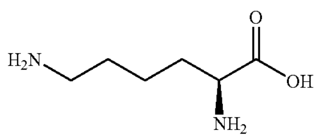 | Lys | K |
| L-arginine | 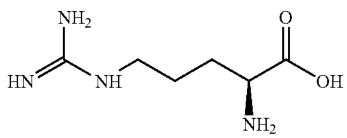 [SMILES: N=C(N)NCCC[C@H](N)C(=O)O] | Arg | R |
| L-histidine | | His | H | wherein each of AA and AA' may independently represent homopolymers of one amino acid from Table 1 or may independently represent heteropolymers of different amino acids selected from Table 1;

"n" and "m" are independently an integer from 0 to about 20; preferably integers from 0 to about 10; and more preferably integers from 0 to about 5;

X represent a non natural amino acid of formula II or a peptide fragment comprising one or more non natural amino acids of formula II optionally including one or more natural amino acids:

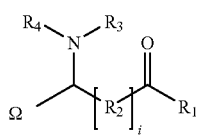

II where $R_1$ represents a peptide bond to an adjacent amino acid of the group AA' or, in the case of cyclic peptides, $R_1$ represents a peptide bond to the terminal residue of the group AA or an amino-functionalized side chain of a residue within the group AA, or where X is a terminal amino acid residue of the type m=0, $R_1$ is typically hydroxyl, but may be any other functionality, including, for example, hydrogen, a protecting group, activating group or a lipophilic group such as a moiety selected from the group consisting of substituted or unsubstituted $C_1$ to $C_{20}$ branched, straight chain, or cyclic alkoxy, aryloxy, and the like;

$R_2$, when present, provides amino acids having $NH_2$ groups on carbons atoms other than the α-carbon (the carbon atom adjacent the carboxyl group), including for example, the β or γ carbons, and may therefore be any spacer group and in particular a moiety selected from the group consisting of substituted or unsubstituted branched or straight chain $C_1$-$C_6$ alkyl, alkenyl, alkynyl, aryl, heteroaryl, or alkyl-aryl groups, including without limitation, linear alkyl moieties of the form —$(CH_2)_a$— where "a" is an integer from 1 to 10, including, for example, —$CH_2$—, —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 10, including for example, —$CH_2O$— or —$OCH_2$—, —$CH_2CH_2O$— or —$OCH_2CH_2$—, —$CH_2CH_2CH_2O$— or —$OCH_2CH_2CH_2$—; —$O(CH_2)_aO$— where "a" is as defined above; or a moiety of the form —$(CH_2)_bO(CH_2)_c$—, —$(CH_2)_bS(CH_2)_c$—, or —$(CH_2)_bNR^a(CH_2)_c$— wherein "b" and "c" are independently an integer from 0 (zero) to 10 and $R^a$ is an alkyl, alkenyl, alkynyl, aryl, heteroaryl, or alkyl-aryl group, and the like. Preferably, $R_2$, when present, is —$CH_2$— or —$CH_2CH_2$—;

"i" represents an integer from 0 (zero) to 3 and will be zero where the amino acid has the α-amino configuration of a natural amino acid;

$R_3$ and $R_4$ may independently represent bonds to adjacent amino acids or may independently selected from the group consisting of hydrogen, substituted or unsubstituted branched or straight chain $C_1$-$C_{20}$ alkyl, alkenyl, alkynyl, aryl, heteroaryl, alkyl-aryl groups, acyl, or N-protecting groups, and will preferably be hydrogen, methyl, ethyl, propyl, acetyl, or, in the case where X is a terminal residue of the type n=0, $R_3$ and $R_4$ are each preferably hydrogen, acetyl, N-protecting group, or a lipophilic group such as a moiety selected from the group consisting of substituted or unsubstituted $C_1$ to $C_{20}$ branched, straight chain, or cyclic alkyl, alkenyl, aryl, heteroaryl, and the like or substituted or unsubstituted $C_1$ to $C_{20}$ branched or straight chain acyl; or $R_3$ and $R_4$ together may form a cyclic alkyl, aryl, heteroalkyl, or heteroaryl, group having between 3 and 6 carbon atoms; or $R_3$ and $R_4$ may independently, together with $R_2$ or $\Omega$ form a cyclic alkyl, aryl, heteroalkyl, or heteroaryl, group having between 3 and 6 carbon atoms (analogous to the natural amino acid proline);

$\Omega$ is selected from hydrogen; hydroxyl; amino; halogen; caboxy, carboxamide, substituted or unsubstituted branched, straight chain or cyclic $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, bicyclic alkyl, aryl, or heteroaryl, and combinations thereof; wherein the foregoing radicals may be substituted with any moiety, including, for example, alkyl, aryl, heteroaryl, hydroxyl; amino; cyano; halogen; oxo, oxa, caboxy, carboxamide, and combinations thereof; with the proviso that X does not represent a naturally occurring amino acid.

$\Omega$ may be selected from or may include one or more substituents selected from the group consisting of aceanthrenyl, aceanthrylenyl, acenaphthenyl, acenaphthenylene, acenaphthenylidene, acenaphthylenyl, acephenanthrenyl, acephenanthrylenyl, acetamido, acetimidoyl, acetoacetyl, acetohydrazonoyl, acetohydroximoyl, acetonyl, acetonylidene, acetoxy, acetyl, acetylamino, acetylhydrazino, acetylamino, acridinyl, acryloyl, adipoyl, alanyl, b-alanyl, allophanoyl, allyl, allylidene, allyloxy, amidino, amino, aminomethyleneamino, aminooxy, ammonio, anilino, anisidino, anisoyl, anthraniloyl, anthryl, anthrylene, arginyl, asparaginyl, aspartoyl, a-aspartyl, b-aspartyl, atropoyl, azabicyclo[2.2.1]heptyl, azelaoyl, azi, azido, azino, azo, azoxy, azulenyl, benzamido, benzeneazo, benzeneazoxy, benzoyl, 1,2-benzenedicarbonyl, 1,3-benzenedicarbony, 1,4-benzenedicarbony, benzenesulfinyl, benzenesulfonamido, benzenesulfonyl, benzenesulfonylamino, benzenetriyl, benzhydryl, benzhydrylidene, benzidino, benziloyl, benzimidazolyl, benzimidoyl, benzofuranyl, benzopyranyl, benzoquinonyl, benzo[b]thienyl, benzoxazinyl, benzoxazolyl, benzoyl, benzoylamino, benzoylhydrazino, benzoylimino, benzoyloxy, benzyl, benzylidene, benzylidyne, benzyloxy, benzyloxycarbonyl, benzylthio, bicyclo[2.2.1]hept-5-en-2-yl, bi(cyclohexan)yl, bi(cyclohexyl)yl, binaphthalenyl, binaphthylyl, biphenylenyl, biphenylyl, bornenyl, bornyl, bornylyl, bromo, bromoformyl, bromonio, butadienyl, butanedioyl, butanediylidene, butanediylidyne, 1,2,3-butanetricarbonyl, butanoyl, 1-butanyliden-4-ylidynes, cis-butenedioyl, trans-butenedioyl, butenoyl, 1-butenyl, 2-butenyl, 2-butenylene, butenylidene, butenylidyne, butoxy, sec-butoxy, tert-butoxy, butyl, sec-butyl, tert-butyl, butylidene, sec-butylidene, butylidyne, butyryl, camphoroyl, camphyl, carbamoyl, carbazido, carbazolyl, carbazono, carbazoyl, carbodiazono, carbolinyl, carbonimidoyl, carbonohydrazido, carbonyl, carbonyldioxy, carboxy, carboxylato, carenyl, caryl, chloro, chlorocarbonyl, chloroformyl, chloronio, chlorosyl, chlorothio, chloryl, cholanthrenyl, chromanyl, chromenyl, chrysenyl, cinnamoyl, cinnamyl, cinnmylidene, cinnolinyl, citraconoyl, coronenyl, crotonoyl, crotyl, cumenyl, cyanato, cyano, cyclobutyl, cycloheptyl, cyclohexadienyl, cyclohexadienylene, cyclohexadienylidene, cyclohexanecarbohydrazonoyl, cyclohexanecarbohydroximoyl, cyclohexanecarbonyl, cyclohexanecarbothioyl, cyclohexanecarboxamide, cyclohexanecarboximidoyl, cyclohexenyl, cyclohexenylene, 2-cyclohexenylidene, cyclohexyl, cyclohexylcarbonyl, cyclohexylene, cyclohexylidene, cyclohexylthiocarbonyl, cyclopentadienyl, cyclopentadienylidene, cyclopentanespirocyclobutyl, cyclopenta[a]phenanthryl, 1,2-cyclopentenophenanthryl, cyclopentenyl, cyclopentenylidene, cyclopentyl, cyclopentylene, cyclopentylidene, cyclopropyl, cystathionyl, cysteinyl, cystyl, decanedioyl, decanoyl, decyl, diacetoxyiodo, diacetylamino, diaminomethyleneamino, diazaanthryl, diazo, diazoamino, dibenzoylamino, dichloroiodo, diethylamino, 3,4-dihydroxybenzoyl, 2,3-dihydroxybutanedioyl, dihydroxyiodo, 2,3-dihydroxypropanoyl, 3,4-dimethoxybenzoyl, 3,4-dimethoxyphenethyl, 3,4-dimethoxyphenylacetyl, dimethylamino, dimethylbenzoyl, dioxacyclohexyl, dioxy, diphenylamino, diphenylmethyl, diphenylmethylene, dithianaphthyl, dithio, dithiocarboxy, dithiosulfo, docosyl, dodecanoyl, dodecyl, dotriacontyl, elaidoyl, epidioxy, epidiseleno, epidithio, epimino, episeleno, epithio, epoxy, ethanedioyl, ethanediylidene, ethanesulfonamido, ethanoyl, etheny, ethoxalyl, ethoxy, ethoxycarbonyl, ethyl, ethylamino, ethylene, ethylenedioxy, ethylidene, ethylidyne, ethylsulfonylamino, ethylthio, ethynyl, ethynylene, fluoranthenyl, fluorenyl, fluorenylidene, fluoro, fluoroformyl, formamido, formimidoyl, formyl, formylamino, formylimino, formyloxy, fumaroyl, furancarbonyl, furazanyl, furfuryl, furfurylidene, furoyl, furyl, 3-furylmethyl, galloyl, geranyl, glutaminyl, glutamoyl, a-glutamyl, g-glutamyl, glutaryl, glyceroyl, glycoloyl, glycyl, glycylamino, glyoxyloyl, guanidino, guanyl, hectyl, henicosyl, hentriacontyl, heptacenyl, heptacontyl, heptacosyl, heptadecanoyl, heptadecyl, heptalenyl, heptanamido, heptanedioyl, heptanoyl, heptaphenyl, heptyl, hexacenyl, hexacontyl, hexacosyl, hexadecanoyl, hexadecyl, hexamethylene, hexanamido, hexanedioyl, hexanimidoyl, hexanohydrazonoyl, hexanohydroximoyl, hexanoyl, hexanoylamino, hexapheneyl, hexyl, hexylidene, hexylidyne, hexyloxy, hippuroyl, histidyl, homocysteinyl, homoseryl, hydantoyl, hydratropoyl, hydrazi, hydrazino, hydrazo, hydrazono, hydroperoxy, hydroseleno, hydroxy, hydroxyamino, m-hydroxybenzoyl, o-hydroxybenzoyl, p-hydroxybenzoyl, 2-hydroxybenzyl, 2-hydroxybenzylidene, hydroxyethanoyl, hydroxyimino, 3-hydroxy-3-methoxybenzoyl, 3-hydroxy-2-phenylpropanoyl, hydroxypropanedioyl, 2-hydroxypropanoyl, icosyl, imidazolidinyl, imidazolinyl, imidazolyl, imino, iminomethylamino, indacenyl, indanyl, indazolyl, indenyl, indolinyl, indolinylidene, indolizinyl, indolyl, iodo, iodoformyl, iodonio, iodoso, iodosyl, iodoxy, iodyl, isobenzofuranyl, isobutoxy, isobutyl, isobutylidene, isobutylidyne, isobutyryl, isocarbonohydrazido, isochromanyl, isocoumarinyl, isocrotonoyl, isocyanato, isocyano, isohexyl, isohexylidene, isohexylidyne, isoindolinyl, isoindolyl, isoleucyl, isonicotinoyl, isoxazolyl, isopentyl, isopentylidene, isopentylidyne, isopentyloxy, isophthaloyl, isopropenyl, isopropoxy, isopropyl, p-isopropylbenzoyl, isopropylbenzyl, isopropylidene, isoquinolyl, isoselenocyanato, isosemiccarbazido, isothiazolyl, isothiocyanato, isothioureido, isoureido, isovaleryl, isoviolanthrenyl, lactoyl, lanthionyl, lauroyl, leucyl, linalyl, lysyl, maleoyl, malonyl, maloyl, menthenyl, menthyl, mercapto, mesaconoyl, mesityl, mesoxalo, mesoxalyl, mesyl, methacryloyl, methaneazo, methaneazoxy, methanesulfinamido, methanesulfinyl, methanesulfonamido, methanesulfonyl, methanoyl, methionyl, methoxalyl, methoxy, methoxybenzoyl, methoxycarbonyl, methoxyimino, methoxyphenyl, methoxysulfinyl, methoxysulfonyl, methoxy(thiosulfonyl), methyl, a-methylacryloyl, methylallyl, methylamino, methylazo, methylazoxy, methylbenzenecarbonoyl, a-methylbenzyl, methylbenzyl, 3-methylbutanoyl, cis-methylbytenedioyl, trans-methylbytenedioyl, methyldithio, methylene, methylenedioxy, 3,4-methylenedioxybenzoyl, 5-methylhexyl, methylidyne, 1-methylpentyl, 2-methylpentyl, 2-methylpropenoyl, methylsulfinimidoyl, methylsulfinohydrazonoyl, methylsulfinohydroximoyl, methylsulfinyl, methylsulfinylamino, methylsulfonimidoyl, methylsulfonohydrazonoyl, methylsulfonohydroxamoyl, methylsulfonyl, methylthio, (methylthio)sulfonyl, 1-methylvinyl, morpholino, morpholinyl, myristoyl, naphthacenyl, naphthaleneazo, naphthalenecarbonyl, naphthalenetetrayl, naphtho[2,3-b]thienyl, naphthoyl, naphthoyloxy, naphthyl, naphthylazo, naphthylene, naphthylenebisazo, naphthylmethylene, naphthylmethylidyne, naphthyloxy, naphthyridinyl, neopentyl, neryl, nicotinoyl, nitrilo, nitro, aci-nitro, nitroso, nonacontyl, nonacosyl, nonadecyl, nonanedioyl, nonanoyl, nonyl, norbornyl, norbornylyl, norcamphyl, norcaryl, norleucyl, norpinanyl, norvalyl, octacontyl, octacosyl, octadecanoyl, cis-9-octadecenoyl, octadecyl, octanedioyl, octanoyl, octyl, oleoyl, ornithyl, ovalenyl, oxalaceto, oxalacetyl, oxa, oxalo, oxalyl, oxamoyl, oxapyrenyl, oxazinyl, oxazolidinyl, oxazolinyl, oxazolyl, oxido, oxo, oxonio, oxy, palmitoyl, pentacenyl, pentacontyl, pentacosyl, pentadecanoyl, pentadecyl, pentafluorothio, pentalenyl, pentamethylene, pentanedioyl, pentanoyl, pentapheneyl, pentazolyl, pentenyl, 2-penten-4-ynyl, pentyl, tert-pentyl, pentylidene, pentylidyne, pentyloxy, perchloryl, perimidinyl, perylenyl, phenacyl, phenacylidene, phenalenyl, phenanthridinyl, phenanthrolinyl, phenanthryl, phenanthrylene, phenarsazinyl, phenazinyl, phenethyl, phenetidino, phenothiazinyl, phenoxathiinyl, phenoxazinyl, phenoxy, phenyl, phenylacetyl, phenylazo, phenylazoxy, phenylcarbamoyl, phenylene, phenylenebisazo, phenylimino, 2-phenylpropanoyl, 3-phenylpropenoyl, 3-phenylpropyl, phenylsulfamoyl, phenylsulfinyl, phenyl sulfonyl, phenylsulfonylamino, phenylthio, 3-phenylureido, phthalamoyl, phthalazinyl, phthalidyl, phthalidylidene, phthalimido, phthaloyl, phytyl, picenyl, picryl, pimeloyl, pinanyl, pinanylene, pinanylidene, piperazinyl, piperidino, piperidyl, piperdylidene, piperonyl, piperonylidene, piperonyloyl, pivaloyl, pleiadenyl, polythio, prolyl, propanedioyl, propane-1,3-diyl-2-ylidene, propane-1,2,3-triyl, propanoyl, propan-1-yl-3-ylidene, propargyl, propenpyl, 1-propenyl, 2-propenyl, propenylene, propioloyl, propionamido, propionyl, propionylamino, propionyloxy, propoxy, propyl, propylene, propylidene, propylidyne, propynoyl, 1-propynyl, 2-propynyl, protocatechuoyl, pteridinyl, purinyl, pyranthrenyl, pyranyl, pyranylidene, pyrazinyl, pyrazolidinyl, pyrazolinyl, pyrazolyl, pyrenyl, pyridazinyl, 2-pyridinecarbonyl, 3-pyridinecarbonyl, 4-pyridinecarbonyl, pyridinio, pyridyl, 2-pyridylcarbonyl, pyridyloxy, pyrimidinyl, pyrrolidinyl, pyrrolinyl, pyrrolyl, pyruvoyl, quinazolinyl, quinolinediyl, quinolizinyl, quinolyl, quinoxalinyl, quinuclidinyl, rubicenyl, salicyl, salicylidene, salicyloyl, sarcosyl, sebacoyl, seleneno, selenino, seleninyl, seleno, selenocyanato, selenoformyl, selenonio, selenono, selenonyl, selenoureido, selenoxo, semicarbazido, semicarbazono, seryl, stearoyl, styryl, suberoyl, succinamoyl, succinimido, succinimidoyl, succinyl, sulfamoyl, sulfanilamido, sulfanilyl, sulfenamoyl, sulfeno, sulfido, sulfinamoyl, sulfino, sulfinyl, sulfo, sulfoamino, sulfonato, sulfonio, sulfonyl, sulfonyldioxy, tartaroyl, tartronoyl, tauryl, telluro, (tercyclohexan)yl, terephthaloyl, terphenylyl, (terthiophen)yl, tetracontyl, tetracosyl, tetradecanoyl, tetradecyl, tetramethylene, tetraphenylenyl, tetrazolyl, thenoyl, thenyl, thenylidene, thianthrenyl, thiazinyl, thiazolidinyl, thiazolinyl, thiazolyl, thienyl, thio, thioacetyl, thiobenzoyl, thiocarbamoyl, thiocarbazono, thiocarbodiazono, thiocarbonohydrazido, thiocarbonyl, thiocarboxy, thiocyanato, thioformyl, thionaphthenyl, thiophanthrenyl, thiophenecarbonyl, thiosemicarbazido, thiosulfino, thiosulfo, thioureido, thioxo, threonyl, thujenyl, thujyl, thyronyl, toluenesulfonyl, toluidino, toluoyl, tolyl, tolylsulfonyl, tosyl, triacontyl, triazano, triazaphenanthryl, triazeno, triazinyl, triazolidinyl, triazolyl, trichlorothio, tricosyl, tridecanoyl, tridecyl, trifluorothio, 3,4,5-trihydroxybenzoyl, trimethylammonio, trimethylanilino, 1,2,2-trimethyl-1,3-cyclopentanedicarbonyl, trimethylene, trimethylenedioxy, trinaphthylenyl, triphenylenyl, triphenylmethyl, trithiadiazaindenyl, trithio, trithiosulfo, tritriacontyl, trityl, tropoyl, tryptophyl, tyrosyl, undecanoyl, undecyl, ureido, ureylene, valeryl, valyl, vanilloyl, vanillyl, vanillylidene, veratroyl, veratryl, veratrylidene, vinyl, vinylene, vinylidene, violanthrenyl, xanthenyl, xylidino, xylyl, and the like.

In certain embodiments, Ω represents an alkyl, alkenyl, or alkynyl radical optionally substituted with hetero atoms. Suitable radicals include, but are not limited to methyl, ethyl, propyl, iso-propyl, butyl, iso-butyl, sec-butyl, tert-butyl, penyl, hexyl, vinyl, allyl, and the structures shown below:

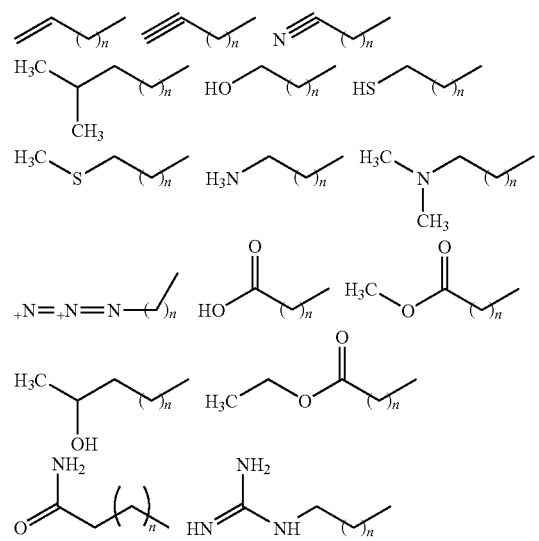

In another embodiment, Ω represents a cyclic alkyl radical optionally substituted with hetero atoms. Non-limiting examples of such cyclic alkyl radicals include:

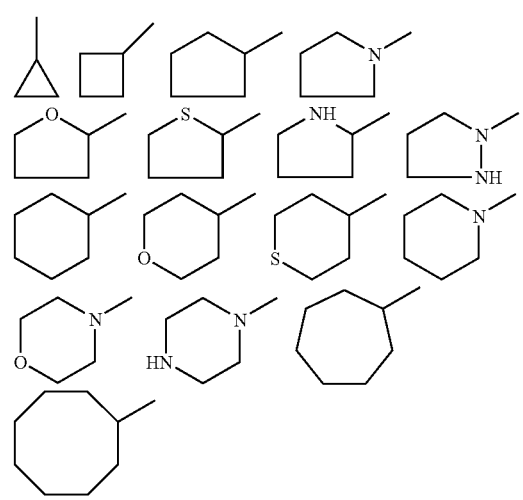

In other embodiments, Ω represents an aryl or heteroaryl substituent, including but not limited to:

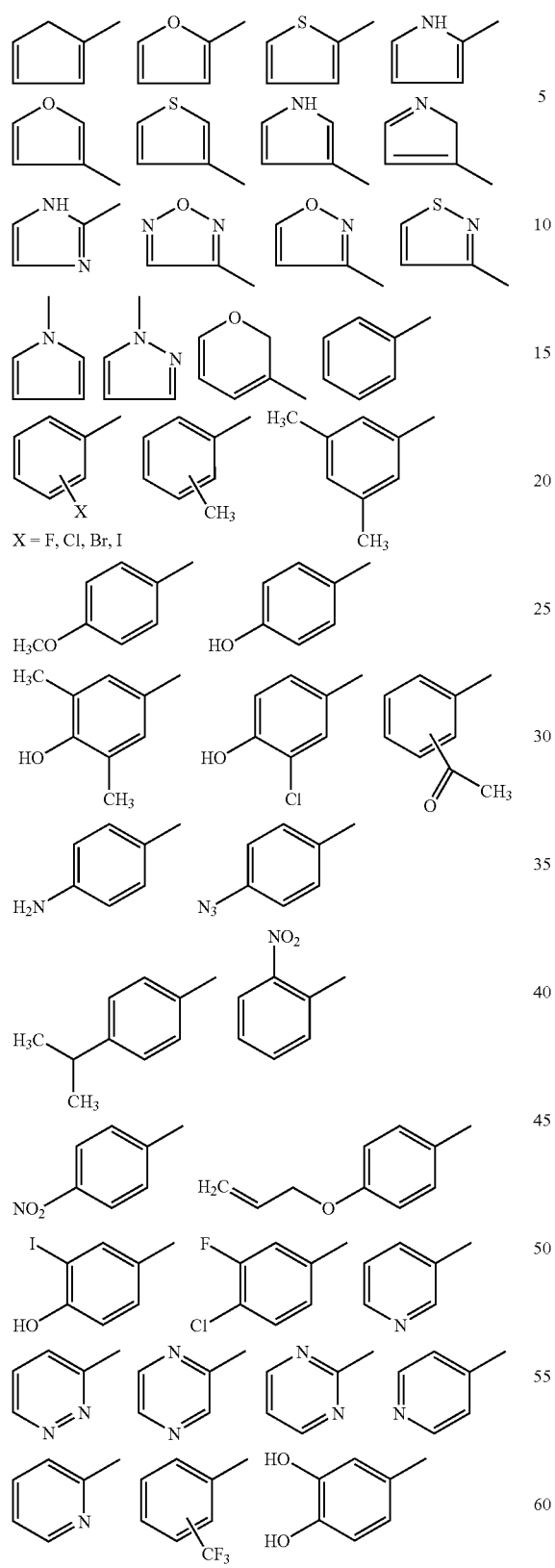
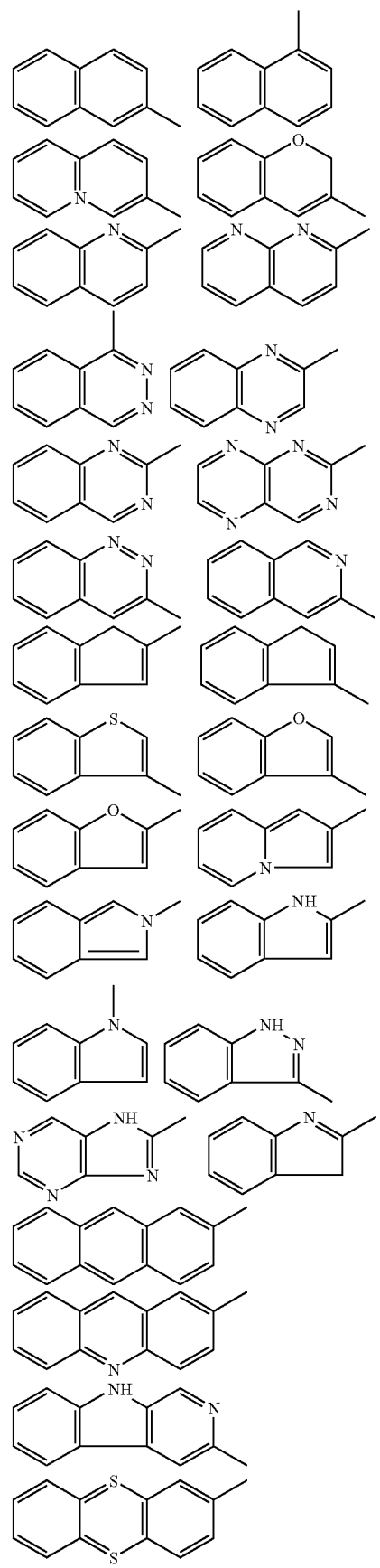
In addition to the foregoing aromatic moieties, Ω may comprise fused aryl or heteroaryl rings, including but not limited to:

-continued

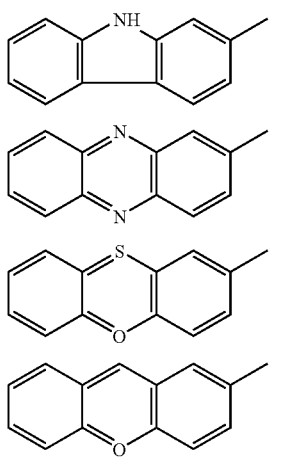

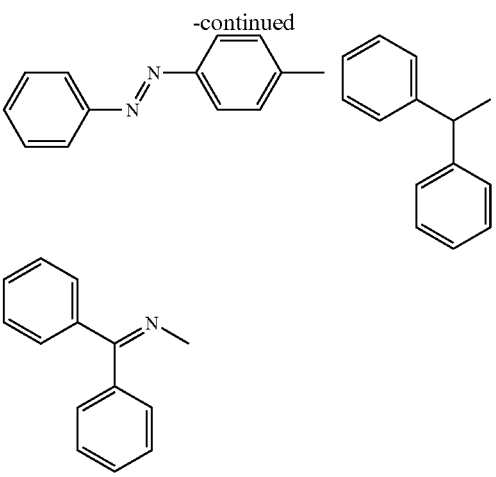

The foregoing radicals are merely representative of the numerous alkyl and aryl substituents which are contemplated to be suitable. Other interesting radicals for Ω include:

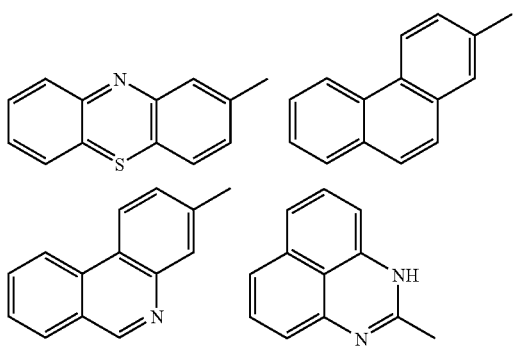

Ω may further include spacer moieties linking any of the foregoing radicals to the carbon atom of the main chain, including for example spacers of the form —(CH$_2$)$_a$— where "a" is an integer from 1 to 10, including, for example, —CH$_2$—, —CH$_2$CH$_2$, —CH$_2$CH$_2$CH$_2$—, or —CH$_2$CH$_2$CH$_2$CH$_2$—; linear alkoxy moieties of the general form —(CH$_2$)$_a$O— or —O(CH$_2$)$_a$— where "a" is an integer from 1 to 10, including for example, —CH$_2$O— or —OCH$_2$—, —CH$_2$CH$_2$O— or —OCH$_2$CH$_2$—, —CH$_2$CH$_2$CH$_2$O— or —OCH$_2$CH$_2$CH$_2$—; —O(CH$_2$)$_a$O— where "a" is an integer from 1 to 10; or a moiety of the form —(CH$_2$)$_b$O(CH$_2$)$_c$—, —(CH$_2$)$_b$S(CH$_2$)$_c$—, or —CH$_2$)$_b$NR$^a$(CH$_2$)$_c$— wherein "b" and "c" are independently an integer from 0 (zero) to 10 and R$^a$ is an alkyl, alkenyl, alkynyl, aryl, heteroaryl, or alkyl-aryl group, and the like.

In selecting suitable substituents for Ω, it may be desirable to employ biosteric substitutions for the side chains of the natural amino acids. For example, a biosterism of phenylalanine provides the interesting non-natural amino acids thienylalanine, furanylalanine, pyridinylalanine, and the like.

X may also comprise variants of the naturally occurring amino acids having inverted chirality at the α-carbon, including D-alanine, D-valine, D-leucine, D-isoleucine, D-proline, D-tryptophan, D-phenylalanine, D-methionine, D-serine, D-tyrosine, D-threonine, D-cysteine, D-asparagine, D-glutamine, D-aspartic acid, D-glutamic acid, D-lysine, D-arginine, and D-histidine; or, in the case of isoleucine and threonine, interesting non-natural amino acids are the [R,R], [S,S], [S,R], and [R,S] diastereomers.

The non-natural amino acids may also be based on the β analogs of natural amino acids as described in, for example, D. Seebach, et al., *Helv. Chim. Acta* 1998, 81, 932, D. Seebach, et al., Helv. Chim. Acta 1996, 79, 913, the disclosures of which are hereby incorporated by reference. The β analogs are provided by Formula II in the case where R$_2$=—CH$_2$— and i=0.

The non-natural amino acids disclosed in U.S. Patent Application Pub. 2004/0121438 A1, the disclosure of which is hereby incorporated by reference, are contemplated to be useful in the practice of the invention. These include beta-alanine (b-Ala); 3-aminopropionic acid (Dap); 2,3-diaminopropionic acid (Dpr); 4-aminobutyric acid, epsilon-aminoisobutyric acid (Aib); epsilon-aminohexanoic acid (Aha); 5-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (Me-Val); homocysteine (hCys) and homoserine (hSer).

A currently preferred peptide according to Formula I is KAvaK defined by (AA)=L-lysine (K), (AA')=L-lysine (K), n and m=1, and X=5-aminovaleric acid (Ava):

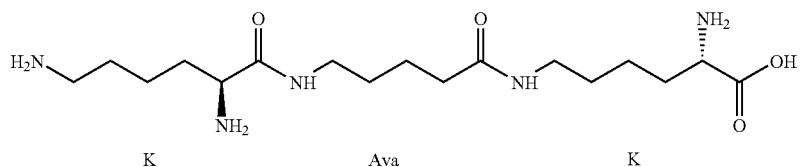

K           Ava           K

In another interesting embodiment of the peptides of formula I, AA and AA' may independently represent a non-naturally occurring amino acid of formula II, or AA and AA' may independently represent a peptide fragment comprising one or more non-naturally occurring amino acids defined by formula II. In a further embodiment, any of AA, AA', and X may further include spacer groups which are not amino acids disposed between adjacent amino acid residues. When present, the spacer groups are typically selected from substituted or unsubstituted branched or straight chain C$_1$-C$_6$ alkyl, alkenyl, alkynyl, aryl, heteroaryl, alkyl-aryl, alkyl-aryl-alkyl, and aryl-alkyl-aryl groups, including without limitation, linear alkyl moieties of the form —(CH$_2$)$_a$— where "a" is an integer from 1 to 20, including, for example, —CH$_2$—, —CH$_2$CH$_2$—, —CH$_2$CH$_2$CH$_2$—, or —CH$_2$CH$_2$CH$_2$CH$_2$—; linear alkoxy moieties of the general form —(CH$_2$)$_a$O— or —O(CH$_2$)$_a$— where "a" is an integer from 1 to 20, including for example, —CH$_2$O— or —OCH$_2$—, —CH$_2$CH$_2$O— or —OCH$_2$CH$_2$—, —CH$_2$CH$_2$CH$_2$O— or —OCH$_2$CH$_2$CH$_2$—; —O(CH$_2$)$_a$O— where "a" is as defined above; or a moiety of the form —(CH$_2$)$_b$O(CH$_2$)$_c$—, —(CH$_2$)$_b$S(CH$_2$)$_c$—, or —CH$_2$)$_b$NR$^a$(CH$_2$)$_c$— wherein "b" and "c" are independently an integer from 0 (zero) to 20 and R$^a$ is an optionally substituted alkyl, alkenyl, alkynyl, aryl, heteroaryl, or alkyl-aryl group; and wherein the spacer group optionally includes fictionalization at either terminal end, or both terminal ends, with functional groups selected from the group consisting of —O—, —S—, —NR$^a$—, NR$^a$—(C=O)—, —O—(C=O)—, —O—(C=O)—O—, and —O—(SO$_2$)—, and the like, where R$^a$ is as defined above.

In another aspect of the invention, peptides are selected from the groups consisting of: (i) peptides comprising one or more amino acids of formula II; (ii) peptides comprising only amino acids of formula II; (iii) peptides comprising one or more amino acids of formula II and further including one or more spacer moieties as defined above; and (iv) peptides comprising only amino acids of formula II and further including one or more spacer moieties as defined above.

It will be understood that peptides other than those of formula I are also within the scope of the invention. For example, any peptide-containing molecule comprising at least one amino acid of formula II are contemplated to be useful in the practice of the invention.

It is well within the skill in the art to prepare peptides comprising non-natural amino acids using, for example, conventional protection and activation chemistry. Typically, the amino functionality of a first amino acid is protected with a removable amino protecting group and the carboxyl functionality of a second amino acid is protected with a removable carboxyl protecting group. Suitable amine protecting groups include, without limitation, benzoyloxycarbonyl (Cbz), tert-butoxycarbonyl (t-Boc), and 9-flourenylmethloxycarbonyl (FMOC). The carboxyl group may be protected protecting by forming an acid or base labile ester such as a methyl, ethyl, benzyl, or trimethylsilyl esters. After protection, the first and second amino acids are reacted in a suitable solvent such as water or DMF in the presence of an in situ activating agent such as N,N'-dicyclohexylcarbodiimide (DCCI), diisopropylcarbodiimide (DIPCDI), or 1-ethyl-3-(3'-dimethylaminopropyl)carbodiimide (EDCI) to effect peptide bond formation. Reactive moieties on the side chains of either amino acid are protected with protecting groups such as tert-butyl or benzyl for OH and SH; methyl, ethyl, tert-butyl or benzyl for carboxyl groups, 2,2,5,7,8-pentamethylchroman-6-sulphonyl for the —NHC(NH$_2$)=NH functionality of Arg, and trityl for the imidazole group of His. Following the coupling reaction, selective deprotection of the amino group of the first amino acid is accomplished by acid hydrolysis under conditions that do not remove the carboxyl protecting group of the second amino acid. The procedure is repeated with a additional amino protected amino acids. Solid phase synthesis, such as the well-known Merrifield method, is especially useful for synthesizing the peptides of the invention.

The incorporation of non-natural amino acids into peptides is described in Hohsaka T, Sisido M "Incorporation of non-natural amino acids into proteins" *Curr. Opin. Chem. Biol.* 6: 809-815 (2002); Noren C J et al. "A general method for site-specific incorporation of unnatural amino acids into proteins" *Science* 244: 182-188 (1989); and Hodgson, David R. W., Sanderson, John M., "The Synthesis of Peptides and Proteins Containing Non-Natural Amino Acids", *Chem. Soc. Rev.*, 2004, 33, 422-430, the disclosures of which are hereby incorporated by reference.

The invention also provides a method for screening a peptide of Formula I for a cosmeceutical activity of interest. The method comprises the steps of (1) measuring the activity of a naturally occurring peptide or peptide comprising only natural amino acids using an assay capable of quantifying said activity; (2) providing a peptide of Formula I having substantial homology to the peptide of step (1) but differing in the substitution of a non-natural amino acid based on the above-described design considerations; (3) measuring the same activity of the peptide from step (2); and (4) comparing the measured activity of the peptides from steps (1) and (3) to determine whether the peptide of step (2) has the activity of interest. Representative cosmeceutical activities include those described herein, for example, inhibition of ACE, inhibition of proteolytic enzymes, melanogenesis-stimulating properties, anti-inflammatory properties, induction of collagen and/or glycosaminoglycans synthesis, stimulation of melanogenesis, Substance P antagonism, as well as those described in U.S. Pat. No. 6,043,218, the disclosure of which is hereby incorporated by reference, and other activities known in the art.

ii. Cosmetic Compositions

The peptides of the invention are provided in cosmetically acceptable vehicle. The vehicle may be either hydrophobic or hydrophilic. Suitable, hydrophobic carriers include, for example, waxy non-ionic substances commonly used in cosmetics, such as esters and ethers of fatty alcohols and of fatty acids, with carbon chain length from $C_4$ to $C_{22}$, preferably from $C_8$ to $C_{18}$, and most preferably from $C_{12}$ to $C_{18}$.

Examples of a fatty hydrophobic carriers include isopropyl myristate, isopropyl palmitate, octyl palmitate, isopropyl lanolate, acetylated lanolin alcohol, the benzoate of $C_{12}C_{15}$ alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate, isopropyl isostearate, and the like.

Suitable hydrophilic carrier solutions can be, for example, glycols and alkoxylated glycols commonly used in cosmetics, including ethylene glycol, diethylene glycol, triethylene glycol, propylene glycol, dipropylene glycol, and the like.

The cosmetic compositions may be formulated as creams, lotions, serums, sprays, sticks and other forms known to those skilled in the art. Creams and lotions are the currently preferred product forms.

The concentration of peptides in the cosmetically acceptable vehicle may range from 1 ppb to 10,000 ppm, preferably from 10 ppb to 1,000 ppm, more preferably from 100 ppb to 100 ppm, and most preferably from 1 ppm to 100 ppm.

The cosmetic compositions will typically comprise the carrier solution described above at levels between about 0.01% and about 90% by weight, preferably between about 0.1% and about 50%, more preferably between about 0.1% and about 20%, and more preferred still between about 1% and about 10% by weight.

Optionally, the present topical composition may include one or more of the invention compositions may optionally comprise other active and inactive ingredients, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. In addition to the foregoing, the personal care products of the invention may contain any other compound for the treatment of skin disorders.

The invention also provides a method for ameliorating and/or preventing signs of human skin photo- and intrinsic aging comprising topically applying the cosmetic compositions of the invention. The cosmetic compositions of the invention are preferably applied to affected skin areas once or twice daily for as long as is necessary to achieve desired anti-aging results.

EXAMPLES

The following examples are meant to demonstrate certain aspects of the invention in a non-limiting fashion.

Example 1

Fibronectin is a homodimer, with two subunits of MW 250K, linked by a disulfide bridge. Fibronectin binds to receptor proteins called integrins that span the cell membrane, and also binds to extracellular matrix components such as collagen, fibrin and heparin. Fibronectin is an important constituent of extracellular matrix and mediates the attachment of cells to cells and to the extracellular matrix. Fibronectin is essential for the maintenance of skin integrity. Fibronectin, important for skin repair, is increased during wound healing process. UV radiation increases the degradation of fibronectin in skin. In addition, fibronectin was found at decreased levels in the papillary dermis of aging skin. See Ray D. et al. *J Biol Chem.* 2006, 281:23060-5; Labat-Robert J. et al. *J Photochem Photobiol* B. 2000 57(2-3):113-8; Pieraggi M T et al. *Ann Pathol.* 1984, 4(3):185-94; Clark R A et al. *J Invest Dermatol.* 1982, 79(5):264-9; and Clark R A *J Invest Dermatol.* 1983, 81(6):475-9. Thus increasing fibronectin levels in skin cells is expected to help improve the appearance of aging skin, with respect to lines, wrinkles, texture, sagging, laxity and firmness of skin.

Normal Human Dermal Fibroblasts-Adult (Cascade Biologics) were cultured in 12-well tissue culture treated plates and treated for 72 hours in the presence or absence of test actives. Following incubation, the conditioned medium from each treatment was collected in a 1.7 mL microcentrifuge tube and frozen at −80° C. for subsequent analysis. The assay was in the format of a competitive inhibition ELISA.

Human fibronectin was pre-coated on the wells except for one row, which served as a reference. Standards and samples were pre-incubated with polyclonal rabbit antibody to human fibronectin. The polyclonal antibody was bound to the fibronectin in the standard dilutions, and in the sample, if present. The mixture was then transferred to the human fibronectin-coated plate. Free rabbit anti-human fibronectin was bound to the fibronectin on the plate. Goat anti-rabbit IgG HRP-conjugate reacted with bound rabbit anti-fibronectin. When HRP substrate was added, a blue color developed. The reaction was stopped by the addition of an acid, changing the color to yellow. This color was quantitated using a microplate reader set at 450 nm. The intensity of the color was inversely proportional to the amount of fibronectin in the original sample.

Summary of Results:

| Active Agent | Concentration | Percent Stimulation of Fibronectin over control |
|---|---|---|
| Palmitoyl Lysyl Aminovaleroyl Lysine | 0.001% | 21.46%* |
| | 0.0001% | 27.24%* |
| | 0.00001% | 28.29%* |

*P < 0.05 vs. control

Our data clearly show the anti-aging benefits specific to human skin cells that can be obtained upon topical application of the peptide to aging or aged skin and/or mucous membranes. In vitro, KavaK stimulated the human fibroblasts to produce Fibronectin, a crucial and beneficial component of dermal matrix, 28% more compared to untreated control fibroblasts of the same stock. As discussed above, Fibronectin has several beneficial effects on the epidermal cells of skin, as it promotes proliferation, cell migration and differentiation— processes that are slowed down considerably with skin aging. Stimulating the epidermal cells via increased fibronectin production (by the underlying fibroblasts) can lead to improved thickness of epidermis, decreasing the appearance of fine lines, creating a more youthful appearance of the skin.

Example 2

Sirtuins are a family of NAD+dependent deacetylase enzymes that have recently been shown to play a critical role in prolonging lifespan in a broad spectrum of organisms, including mammals (Guarente, 2005 Mechanisms in Ageing and Devt 126:923). In 1986, Weindruch et al (J. Nutr. 1986 116(4):641-54) reported for the first time that restricting the caloric intake of lab mice proportionally increased their lifespan compared to a group of mice with a normal diet. The calorie-restricted mice also maintained a youthful appearance and activity levels longer, and showed delays in age-related diseases. The findings have since been accepted and extended to other animals such as yeast (Lin et al 2002 Nature 418: 344), and nematode worms (Lakowski 1998 PNAS 95: 13091) and Drosophila flies (Clancy et al 2001 Science 292: 104).

Research into the mechanisms of caloric restriction identified the gene Sir2 (Silent Information Regulator 2) which appears to be responsible for mediating the life-extending effects of caloric restriction (Lin et al 2000, Science 2289: 2126). This gene was shown to regulate lifespan in yeast— increasing the dosage of this gene extended lifespan, and loss of function shortened it (Kaeberlein et al 1999, Genes and Devt. 13:2570-2580). SIRT1 is the human homolog of the yeast Sir2 gene and is believed to play a similar role in human cells.

SIRT1 is believed to promote cell survival by binding to the protein p53 and downregulate its activity. An interesting observation is that rodents subjected to caloric restriction are more resistant to certain stressors, like oxidative stress (Sohal and Weindruch 1996 Science 273:59, Masoro 2000 Exp Gerontol. 35:299). This has been linked to the ability of the Sir protein to negatively control p 53. In yeast, Sir2 represses p53-dependent apoptosis in response to DNA damage and oxidative stress, whereas when Sir2 is mutated, it increases the sensitivity of cells to the stress response (Luo et al 2001 Cell 107:137, Vaziri et al 2001 Cell 107:149).

Oxidative stress is believed to be one of the major contributors to aging of tissues and the organism as a whole. In skin, as in other tissues, accumulation of mutations in the genomic as well as mitochondrial DNA (caused by Reactive oxygen species generated during normal metabolic activities) can lead to dysfunctional cells, this can lead to intrinsic aging of the skin. Additionally, in skin, cellular stress due to oxygen free radicals d from exposure to ultraviolet radiation and the resulting damage to proteins, membranes and DNA have been shown to play a key role in extrinsic or photoaging skin.

Thus it is anticipated that upregulation of SIRT1 expression in skin will have a protective effect, serving to extend the lifespan of skin cells and keeping them in a young and healthy state, thus helping to improve the appearance of aging skin. Especially pertinent to skin cells is the fact that cellular longevity means escape from replicative senescence, that is, the cells are able to divide and produce more generations of daughter cells. For the dermal fibroblasts, this means prolonged and increased production of collagen, elastin, and matrix molecules such as hyaluronic acid and fibronectin, all of which are known to decrease in aged skin.

Method: Normal Human Dermal Fibroblasts—Adult (Cascade Biologics)—were cultured in 100 mm dishes and treated for 24 hours with test active or vehicle control at 37° C. with 5% $CO_2$. Each of the treatment plates are harvested for protein collection from whole cell lysates.

Protein from each of the treatments were denatured and run on a SDS-PAGE gel (4 to 15% gradient). The samples were transferred to a membrane for Western blotting, a technique which is capable of detecting Sirtuin-1 and its expression level through the interaction with a primary antibody. This primary antibody then interacts with a secondary antibody that is linked to an enzyme. In a process called enzymatic chemiluminescence (ECL), the linked enzyme (i.e.—Horseradish Peroxidase or HRP) reacts with a substrate making it emit light that can be detected through exposure to film, which is developed using a ECL developing machine. The amount of emitted light is directly proportional to the amount of protein expressed in the cell lysate. Each band seen on the film can be quantified using image quantification software.

The results for the stimulation of the expression of SIRT1 protein in human fibroblasts by KavaK over control are shown below.

| Active Agent | Concentration | Percent Change in expression of SIRT1 protein |
| --- | --- | --- |
| Palmitoyl-KavaK | 0.001% | 102% |

The design of the peptide itself is beneficial, as its nonnatural amino acid, aminovaleric acid, makes it more resistant to breakdown by protease enzymes present in human skin so that it can remain active in the skin longer, and hence stimulate the skin cells more efficiently as compared to peptides that are broken down easily by skin enzymes.

The patents and patent applications referenced herein are hereby incorporated by reference in their entirety.

The invention having been described by the foregoing description of the preferred embodiments, it will be understood that the skilled artisan may make modifications and variations of these embodiments without departing from the spirit or scope of the invention as set forth in the following claims.

The invention claimed is:

1. A method of ameliorating or preventing signs of human skin aging comprising topically applying to the skin a cosmetic composition comprising a peptide having the sequence KavaK and the structure:

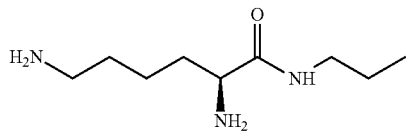

-continued

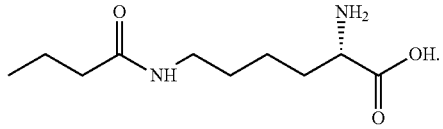

2. A cosmetic composition comprising a peptide and a cosmetically acceptable vehicle, wherein said peptide has the sequence KavaK and the structure:

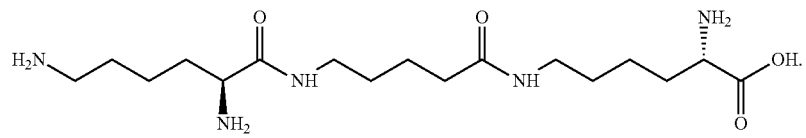 [SMILES: NCCCC[C@H](N)C(=O)NCCCCC(=O)NCCCC[C@H](N)C(=O)O]

3. The cosmetic composition of claim 2, wherein said peptide is present in an amount from 1 ppb to 10,000 ppm.

4. A method for treating, ameliorating, and/or preventing the appearance of fine lines and wrinkles comprising topically applying to skin in need thereof, a cosmetic composition comprising a peptide having the sequence KavaK and the structure:

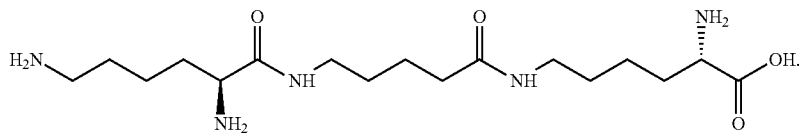

in an amount effective to increase fibronectin levels in skin cells.

5. A method of ameliorating or preventing signs of human skin aging comprising topically applying to the skin a cosmetic composition comprising Palmitoyl Lysyl Aminovaleroyl Lysine.

6. A method for treating, ameliorating, and/or preventing the appearance of fine lines and wrinkles comprising topically applying to skin in need thereof a cosmetic composition comprising Palmitoyl Lysyl Aminovaleroyl Lysine in an amount effective to increase fibronectin levels in skin cells.

7. A cosmetic composition comprising Palmitoyl Lysyl Aminovaleroyl Lysine and a cosmetically acceptable vehicle.

8. The cosmetic composition of claim 6, wherein said Palmitoyl Lysyl Aminovaleroyl Lysine is present in an amount from 1 ppb to 10,000 ppm.

* * * * *

SEQUENCE LISTING

<160> NUMBER OF SEQ ID NOS: 18

<210> SEQ ID NO 1
<211> LENGTH: 4
<212> TYPE: PRT
<213> ORGANISM: Artificial Sequence -continued

```
<220> FEATURE:
<223> OTHER INFORMATION: SYNTHETIC OLIGOPEPTIDE;  H-GQPR-OH

<400> SEQUENCE: 1

Gly Gln Pro Arg
1

<210> SEQ ID NO 2
<211> LENGTH: 4
<212> TYPE: PRT
<213> ORGANISM: Artificial Sequence
<220> FEATURE:
<223> OTHER INFORMATION: SYNTHETIC OLIGOPEPTIDE; PALMITOYL-GQPR-OH

<400> SEQUENCE: 2

Gly Gln Pro Arg
1

<210> SEQ ID NO 3
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 3

Arg Asp Phe Thr Lys Ala Thr Asn Ile Arg Leu Arg Phe Leu Arg
1               5                   10                  15

<210> SEQ ID NO 4
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 4

Leu Asp Ala Pro
1

<210> SEQ ID NO 5
<211> LENGTH: 6
<212> TYPE: PRT
<213> ORGANISM: Artificial Sequence
<220> FEATURE:
<223> OTHER INFORMATION: SYNTHETIC PEPTIDE

<400> SEQUENCE: 5

Lys Leu Asp Ala Pro Thr
1               5

<210> SEQ ID NO 6
<211> LENGTH: 6
<212> TYPE: PRT
<213> ORGANISM: Artificial Sequence
<220> FEATURE:
<223> OTHER INFORMATION: SYNTHETIC PEPTIDE

<400> SEQUENCE: 6

Val Gly Val Ala Pro Gly
1               5

<210> SEQ ID NO 7
<211> LENGTH: 4
<212> TYPE: PRT
<213> ORGANISM: Artificial Sequence
<220> FEATURE:
<223> OTHER INFORMATION: SYNTHETIC PEPTIDE
```

```
<400> SEQUENCE: 7

Val Val Arg Pro
1

<210> SEQ ID NO 8
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 8

Val Val Pro Gln
1

<210> SEQ ID NO 9
<211> LENGTH: 6
<212> TYPE: PRT
<213> ORGANISM: Artificial Sequence
<220> FEATURE:
<223> OTHER INFORMATION: SYNTHETIC PEPTIDE

<400> SEQUENCE: 9

Val Ala Ala Arg Pro Gly
1               5

<210> SEQ ID NO 10
<211> LENGTH: 7
<212> TYPE: PRT
<213> ORGANISM: Artificial Sequence
<220> FEATURE:
<223> OTHER INFORMATION: SYNTHETIC PEPTIDE

<400> SEQUENCE: 10

Leu Gly Ala Gly Gly Ala Gly
1               5

<210> SEQ ID NO 11
<211> LENGTH: 5
<212> TYPE: PRT
<213> ORGANISM: Artificial Sequence
<220> FEATURE:
<223> OTHER INFORMATION: SYNTHETIC PEPTIDE; VGVXaaG; Xaa= Hyp =
      hydroxyproline
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Val Gly Val Xaa Gly
1               5

<210> SEQ ID NO 12
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 12

Lys Thr Thr Lys Ser
1               5
```

```
<210> SEQ ID NO 13
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 13

His Phe Arg Trp
1

<210> SEQ ID NO 14
<211> LENGTH: 6
<212> TYPE: PRT
<213> ORGANISM: Artificial Sequence
<220> FEATURE:
<223> OTHER INFORMATION: SYNTHETIC PEPTIDE; Xaa1= D-Phe; Xaa2= D-His;
      Tyr D-Phe Phe D-His Leu Met -NH2
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Tyr Xaa Phe Xaa Leu Met
1               5

<210> SEQ ID NO 15
<211> LENGTH: 10
<212> TYPE: PRT
<213> ORGANISM: Artificial Sequence
<220> FEATURE:
<223> OTHER INFORMATION: SYNTHETIC PEPTIDE; Xaa1= D-NicLys;  Xaa2= 3-Pal
      Pro; Xaa3= D-Cl2; Xaa4= D-Trp; Xaa5= D-Trp;  Xaa6= Nle; D-NicLys
      Pro 3-Pal Pro D-Cl2 Phe Asn D-Trp Phe D-Trp Leu Nle- NH2
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 15

Xaa Pro Xaa Xaa Asn Xaa Phe Xaa Leu Xaa
1               5                   10

<210> SEQ ID NO 16
<211> LENGTH: 41
<212> TYPE: PRT
<213> ORGANISM: Artificial Sequence
<220> FEATURE:
<223> OTHER INFORMATION: SYNTHETIC PEPTIDE
```

```
<400> SEQUENCE: 16

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Thr Cys Cys Lys Lys Pro
            35                  40

<210> SEQ ID NO 17
<211> LENGTH: 6
<212> TYPE: PRT
<213> ORGANISM: Artificial Sequence
<220> FEATURE:
<223> OTHER INFORMATION: SYNTHETIC PEPTIDE: acetyl hexapeptide-3; Xaa1=
      glutamyl; Xaa2= glutamyl; Xaa3= methyonyl; Xaa4=  glutamyl; Xaa5=
      arginyl; Xaa6= arginylamide
<220> FEATURE:
<221> NAME/KEY: misc_feature
<222> LOCATION: (1)..(6)
<223> OTHER INFORMATION: Xaa can be any naturally occurring amino acid

<400> SEQUENCE: 17

Xaa Xaa Xaa Xaa Xaa Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: SYNTHETIC PEPTIDE:  palmitoyl pentapeptide-3

<400> SEQUENCE: 18

Lys Thr Thr Lys Ser
1               5
```